US008633318B2

(12) United States Patent
Savory et al.

(10) Patent No.: US 8,633,318 B2
(45) Date of Patent: Jan. 21, 2014

(54) COMPOUNDS FOR TREATMENT OR PREVENTION OF INFLAMMATION, AN INFLAMMATORY DISEASE, OR AN IMMUNE OR AN AUTOIMMUNE DISORDER

(75) Inventors: Edward Daniel Savory, Cambourne (GB); Iain David Simpson, Cambridge (GB)

(73) Assignee: Proximagen Ltd, London (GB)

( * ) Notice: Subject to any disclaimer, the term of this patent is extended or adjusted under 35 U.S.C. 154(b) by 0 days.

(21) Appl. No.: 13/062,366

(22) PCT Filed: Sep. 16, 2009

(86) PCT No.: PCT/EP2009/062018
§ 371 (c)(1),
(2), (4) Date: Apr. 26, 2011

(87) PCT Pub. No.: WO2010/031791
PCT Pub. Date: Mar. 25, 2010

(65) Prior Publication Data
US 2011/0195992 A1    Aug. 11, 2011

Related U.S. Application Data

(60) Provisional application No. 61/106,727, filed on Oct. 20, 2008.

(30) Foreign Application Priority Data

Sep. 16, 2008 (SE) ...................... 0801980

(51) Int. Cl.
*A61K 31/4162* (2006.01)
*C07D 471/04* (2006.01)

(52) U.S. Cl.
USPC .......................... 546/119; 514/303

(58) Field of Classification Search
USPC .......................... 514/303; 546/119
See application file for complete search history.

(56) References Cited

U.S. PATENT DOCUMENTS 5,264,576 A * 11/1993 Shutske et al. ................ 546/119

FOREIGN PATENT DOCUMENTS

WO         0238153 A1    5/2002
WO    WO 0238153 A1 *  5/2002

OTHER PUBLICATIONS

Freshney, RI. Culture of Animal Cells: A Manual of Basic Technique. John Wiley and Sons. 2005, 5th Ed., p. 8.*
Dermer, GB. Another Anniversary for the War on Cancer. Bio/Technology. 1994, vol. 12, p. 320.*
Cornelison, TL. Human papillomavirus genotype 16 vaccines for cervical cancer prophylaxis and treatment. Curr. Opin. Oncol. 2000, vol. 12(5), p. 466.*
West, AR. Solid State Chemistry and its Applications. John Wiley and Sons, LTD. 1990, p. 358 and p. 365.*
Bleich, S. et al. Decreased serum semicarbazide sensitive aminooxidase (SSAO) activity in patients with major depression. Progress in Neuro-Psychopharmacology & Biological Psychiatry. 2006, vol. 30, p. 906.*
STN results U.S. Patent 5,264,576, Shutske (1993).*
International Search Report, Nov. 2009.

* cited by examiner

*Primary Examiner* — Yong Chu
*Assistant Examiner* — Sonya Wright
(74) *Attorney, Agent, or Firm* — Banner & Witcoff, Ltd.

(57) ABSTRACT

The present invention relates to compounds of formula (I),

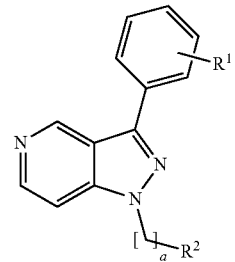

and their pharmaceutically acceptable salts, solvates, hydrates, geometrical isomers, tautomers, optical isomers or N-oxides, which are inhibitors of SSAO activity. The invention further relates to pharmaceutical compositions comprising these compounds and to the use of these compounds for the treatment of medical conditions wherein inhibition of SSAO activity is beneficial, such as such as inflammatory diseases and immune disorders.

7 Claims, No Drawings

COMPOUNDS FOR TREATMENT OR PREVENTION OF INFLAMMATION, AN INFLAMMATORY DISEASE, OR AN IMMUNE OR AN AUTOIMMUNE DISORDER

CROSS REFERENCE TO RELATED APPLICATIONS

This application is a National Stage application of co-pending PCT application PCT/EP2009/062018 filed Sep. 16, 2009, which application claims priority from SE Application No. 0801980-4 filed Sep. 16, 2008, and U.S. Ser. No. 61/106,727 filed Oct. 20, 2008. The above mentioned applications are incorporated herein by reference in their entirety.

FIELD OF THE INVENTION

The present invention relates to new pyrazolo[4,3-c]pyridine compounds of formula (I), which are inhibitors of SSAO activity. The invention also relates to pharmaceutical compositions comprising these compounds and to the use of these compounds in the treatment or prevention of medical conditions wherein inhibition of SSAO activity is beneficial, such as such as inflammatory diseases and immune disorders.

BACKGROUND ART

Semicarbazide-sensitive amine oxidase (SSAO), otherwise known as Vascular Adhesion Protein-1 (VAP-1) or Amine Oxidase, Copper Containing 3 (AOC3), belongs to the is copper-containing amine oxidase family of enzymes (EC.1.4.3.6). Members of this enzyme family are sensitive to inhibition by semicarbazide and utilize cupric ion and protein-derived topa quinone (TPQ) cofactor in the oxidative deamination of primary amines to aldehydes, hydrogen peroxide, and ammonia according to the following reaction:

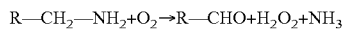

$$R-CH_2-NH_2+O_2 \rightarrow R-CHO+H_2O_2+NH_3$$

Known substrates for human SSAO include endogenous methylamine and aminoacetone as well as some xenobiotic amines such as benzylamine [Lyles, *Int. J. Biochem. Cell Biol.* 1996, 28, 259-274; Klinman, *Biochim. Biophys. Acta* 2003, 1647(1-2), 131-137; Mátyus et al., *Curr. Med. Chem.* 2004, 11(10), 1285-1298; O'Sullivan et al., *Neurotoxicology* 2004, 25(1-2), 303-315]. In analogy with other copper-containing amine oxidases, DNA-sequence analysis and structure determination suggest that the tissue-bound human SSAO is a homodimeric glycoprotein consisting of two 90-100 kDa subunits anchored to the plasma membrane by a single N-terminal membrane spanning domain [Morris et al., *J. Biol. Chem.* 1997, 272, 9388-9392; Smith et al., *J. Exp. Med.* 1998, 188, 17-27; Airenne et al., *Protein Science* 2005, 14, 1964-1974; Jakobsson et al., *Acta Crystallogr. D Biol. Crystallogr.* 2005, 61(Pt 11), 1550-1562].

SSAO activity has been found in a variety of tissues including vascular and non-vascular smooth muscle tissue, endothelium, and adipose tissue [Lewinsohn, *Braz. J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int.* 1998, 33, 415-423; Lyles & Pino, *J. Neural. Transm. Suppl.* 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunol.* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijarvi et al., *J. Immunol.* 1998, 161, 1549-1557]. It has recently been shown that circulating human and rodent SSAO originates from the tissue-bound form [Göktürk et al., *Am. J. Pathol.* 2003, 163(5), 1921-1928; Abella et al., *Diabetologia* 2004, 47(3), 429-438; Stolen et al., *Circ. Res.* 2004, 95(1), 50-57], whereas in other mammals the plasma/serum SSAO is also encoded by a separate gene called AOC4 [Schwelberger, *J. Neural. Transm.* 2007, 114(6), 757-762].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immunol.* 2001, 22, 211-216; Salmi & Jalkanen, in *"Adhesion Molecules: Functions and Inhibition"* K. Ley (Ed.), 2007, pp. 237-251], and might also play a role in connective tissue matrix development and maintenance [Langford et al., *Cardiovasc. Toxicol.* 2002, 2(2), 141-150; Göktürk et al., *Am. J. Pathol.* 2003, 163(5), 1921-1928]. Moreover, a link between SSAO and angiogenesis has recently been discovered [Noda et al., *FASEB J.* 2008, 22(8), 2928-2935].

Several studies in humans have demonstrated that SSAO activity in blood plasma is elevated in conditions such as congestive heart failure, diabetes mellitus, Alzheimer's disease, and inflammation [Lewinsohn, *Braz. J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijärvi et al., *J. Immunol.* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647(1-2), 193-199; Mátyus et al., *Curr. Med. Chem.* 2004, 11(10), 1285-1298; O'Sullivan et al., *Neurotoxicology* 2004, 25(1-2), 303-315; del Mar Hernandez et al., *Neurosci. Lett.* 2005, 384(1-2), 183-187]. The mechanisms underlying these alterations of enzyme activity are not clear. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647(1-2), 193-199; Jiang et al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium [Salmi et al., *Immunity* 2001, 14(3), 265-276; Salmi & Jalkanen, in *"Adhesion Molecules: Functions and Inhibition"* K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., *Eur. J. Immunol.* 2005, 35(11), 3119-3130; Salter-Cid et al., *J. Pharmacol. Exp. Ther.* 2005, 315(2), 553-562; McDonald et al., *Annual Reports in Medicinal Chemistry* 2007, 42, 229-243; Salmi & Jalkanen, in "*Adhesion Molecules: Functions and Inhibition*" K. Ley (Ed.), 2007, pp. 237-251; Noda et al., *FASEB J.* 2008 22(4), 1094-1103; Noda et al., *FASEB J.* 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it therefore seems likely that SSAO inhibitors may be effective anti-inflammatory drugs in a wide range of human diseases.

The invention described here relates to novel pyrazolo[4,3-c]pyridine derivatives as a new class of chemically distinct SSAO inhibitors with biological, pharmacological, and pharmacokinetic characteristics that make them suitable for use as prophylactic or therapeutic agents in a wide range of human inflammatory diseases and immune disorders. This therapeutic capacity is designed to block SSAO enzyme action, reducing the levels of pro-inflammatory enzyme products (aldehydes, hydrogen peroxide and ammonia) whilst also decreasing the adhesive capacity of immune cells and correspondingly their activation and final extra-vasation. Diseases where such an activity is expected to be therapeutically beneficial include all diseases where immune cells play a prominent role in the initiation, maintenance or resolution of the pathology, such as multiple sclerosis, arthritis and vasculitis.

Pyrazolo[4,3-c]pyridine compounds have been disclosed in WO 94/03453 as angiotensin II receptor antagonists for use in the treatment of hypertension and congestive heart failure. EP 594001 describes 4-phenylpyrazolo[4,3-c]pyridine compounds as serotonin reuptake inhibitors for use in the treatment of depression and obsessive competitive disorder. SSAO inhibitors have been described in WO 02/38153, which discloses certain tetrahydroimidazo[4,5-c]pyridine derivatives that are useful in the treatment of diabetes and vascular complications.

DISCLOSURE OF THE INVENTION

It has surprisingly been found that the new pyrazolo[4,3-c]pyridine compounds of formula (I) are inhibitors of SSAO activity. They are therefore useful in the treatment or prevention of diseases in which inhibition of SSAO activity is beneficial. As such they are potentially useful for the treatment or prevention of inflammation, inflammatory diseases, immune or autoimmune disorders. Consequently, the invention relates to a compound of formula (I),

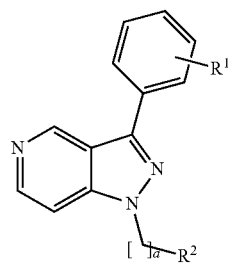

(I)

or a pharmaceutically acceptable salt, solvate, hydrate, geometrical isomer, tautomer, optical isomer or N-oxide thereof, wherein:

$R^1$ is one, two or three substituents independently selected from halogen, cyano, $C_{1-6}$-alkyl, halo-$C_{1-6}$-alkyl and $C_{1-6}$-alkoxy;

$R^2$ is a 4- to 7-membered heterocyclic ring containing 1 or 2 heteroatoms independently selected from O, S and $N(R^3)$, and wherein ring carbon atoms are optionally substituted with $R^4$;

$R^3$ is selected from hydrogen, $C_{1-6}$-alkyl, hydroxy-$C_{1-6}$-alkyl, cyano-$C_{1-6}$-alkyl, halo-$C_{1-6}$-alkyl, $C_{1-6}$-alkoxy-$C_{1-6}$-alkyl, $C_{1-6}$-acyl and $C_{1-6}$-alkylsulfonyl;

$R^4$ is independently selected from halogen, hydroxy, $C_{1-6}$-alkyl, hydroxy-$C_{1-6}$-alkyl, $C_{1-6}$-alkoxy-$C_{1-6}$-alkyl, cyano-$C_{1-6}$-alkyl, halo-$C_{1-6}$-alkyl and $C_{1-6}$-alkoxy; and a is 0, 1 or 2;

provided that the compound is not:
3-(3,4-dichlorophenyl)-1-(1-methylpiperidin-4-yl)-1H-pyrazolo[4,3-c]pyridine, or
1-(1-methylpiperidin-4-yl)-3-[4-(trifluoromethyl)phenyl]-1H-pyrazolo[4,3-c]pyridine.

More preferred compounds of formula (I) are those wherein:

$R^1$ is selected from halogen, cyano and $C_{1-4}$-alkyl; and $R^2$ is a 5- to 6-membered heterocyclic ring containing 1 or 2 heteroatoms independently selected from O, S and $N(R^3)$, and wherein ring carbon atoms are optionally substituted with $R^4$.

A preferred embodiment of the invention consists of compounds of formula (I'),

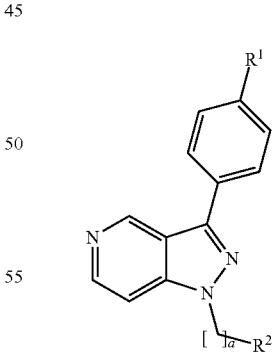

(I')

wherein $R^1$ is selected from halogen, cyano and $C_{1-4}$-alkyl;

$R^2$ is a 5- to 6-membered heterocyclic ring containing 1 or 2 heteroatoms independently selected from O, S and $N(R^3)$, and wherein ring carbon atoms are optionally substituted with $R^4$;

$R^3$ is selected from hydrogen, $C_{1-4}$-alkyl, hydroxy-$C_{1-4}$-alkyl, cyano-$C_{1-4}$-alkyl, halo-$C_{1-4}$-alkyl, $C_{1-4}$-alkoxy-$C_{1-4}$-alkyl, $C_{1-4}$-acyl and $C_{1-4}$-alkylsulfonyl;

R⁴, if present, is independently selected from $C_{1-4}$-alkyl, halo-$C_{1-4}$-alkyl, hydroxy-$C_{1-4}$-alkyl and $C_{1-4}$-alkoxy-$C_{1-4}$-alkyl; and a is 0 or 1.

A further preferred embodiment of the invention consists of compounds of formula (I″),

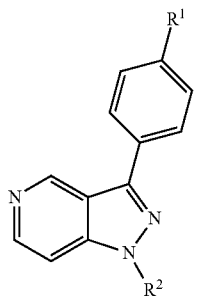

(I″)

wherein R¹ is selected from halogen, cyano and $C_{1-4}$-alkyl;
R² is a saturated 5- to 6-membered heterocyclic ring containing 1 heteroatom selected from O and N(R³), and wherein ring carbon atoms are optionally substituted with R⁴;
R³ is hydrogen, $C_{1-4}$-alkyl or cyano-$C_{1-4}$-alkyl;
R⁴, if present, is independently methyl or ethyl.

Even more preferred compounds of formula (I″) are those wherein:
R¹ is fluoro, chloro or methyl;
R² is a piperidine, tetrahydropyran or tetrahydrofuran ring;
R³, if present, is hydrogen, methyl or cyanomethyl; and
R⁴ is absent.

Specific preferred compounds of the invention are selected from the group consisting of:
3-(4-Fluorophenyl)-1-(tetrahydro-2H-pyran-4-yl)-1H-pyrazolo[4,3-c]pyridine;
3-(4-Chlorophenyl)-2-(tetrahydro-2H-pyran-4-yl)-2H-pyrazolo[4,3-c]pyridine;
3-(4-Methylphenyl)-1-(tetrahydro-2H-pyran-4-yl)-1H-pyrazolo[4,3-c]pyridine;
3-(4-Chlorophenyl)-1-[(3R)-tetrahydrofuran-3-yl]-1H-pyrazolo[4,3-c]pyridine;
3-(4-Chlorophenyl)-1-piperidin-4-yl-1H-pyrazolo[4,3-c]pyridine;
3-(4-Chlorophenyl)-1-(1-methylpiperidin-4-yl)-1H-pyrazolo[4,3-c]pyridine;
{4-[3-(4-Chlorophenyl)-1H-pyrazolo[4,3-c]pyridin-1-yl]piperidin-1-yl}acetonitrile;
3-(4-Chlorophenyl)-1-(tetrahydro-2H-pyran-4-ylmethyl)-1H-pyrazolo[4,3-c]pyridine;
3-(4-Chlorophenyl)-1-[1-(methylsulfonyl)piperidin-4-yl]-1H-pyrazolo[4,3-c]pyridine;
1-(1-Acetylpiperidin-4-yl)-3-(4-chlorophenyl)-1H-pyrazolo[4,3-c]pyridine;
3-(4-Chlorophenyl)-1-[1-(2-methoxyethyl)piperidin-4-yl]-1H-pyrazolo[4,3-c]pyridine;
3-(4-Chlorophenyl)-1-piperidin-3-yl-1H-pyrazolo[4,3-c]pyridine;
3-(4-Chlorophenyl)-1-[(3S)-tetrahydrofuran-3-yl]-1H-pyrazolo[4,3-c]pyridine;
3-(4-Chlorophenyl)-1-(tetrahydrofuran-3-ylmethyl)-1H-pyrazolo[4,3-c]pyridine;
3-(4-Chlorophenyl)-1-(1-ethylpiperidin-4-yl)-1H-pyrazolo[4,3-c]pyridine;
3-(4-Chlorophenyl)-1-(1-isopropylpiperidin-4-yl)-1H-pyrazolo[4,3-c]pyridine;
3-(4-Fluorophenyl)-1-(1-methylpiperidin-4-yl)-1H-pyrazolo[4,3-c]pyridine;
3-(4-Fluorophenyl)-1-piperidin-4-yl-1H-pyrazolo[4,3-c]pyridine;
4-[1-(Tetrahydro-2H-pyran-4-yl)-1H-pyrazolo[4,3-c]pyridin-3-yl]benzonitrile; and
4-[1-(1-Methylpiperidin-4-yl)-1H-pyrazolo[4,3-c]pyridin-3-yl]benzonitrile.

Another object of the present invention is a compound of formula (I) for use in therapy. The compounds as defined above are useful as inhibitors of SSAO activity. As such, they are useful in the treatment or prevention of conditions and diseases in which inhibition of SSAO activity is beneficial. More specifically, they are useful for the treatment or prevention of inflammation, inflammatory diseases, immune or autoimmune disorders.

In particular, it is believed that compounds of formula (I) are useful for the treatment or prevention of arthritis (such as rheumatoid arthritis, juvenile rheumatoid arthritis, osteoarthritis and psoriatic arthritis), synovitis, vasculitis, conditions associated with inflammation of the bowel (such as Crohn's disease, ulcerative colitis, inflammatory bowel disease and irritable bowel syndrome), atherosclerosis, multiple sclerosis, Alzheimer's disease, vascular dementia, pulmonary inflammatory diseases (such as asthma, chronic obstructive pulmonary disease and acute respiratory distress syndrome), fibrotic diseases (including idiopathic pulmonary fibrosis, cardiac fibrosis and systemic sclerosis (scleroderma)), inflammatory diseases of the skin (such as contact dermatitis, atopic dermatitis and psoriasis), systemic inflammatory response syndrome, sepsis, inflammatory and/or autoimmune conditions of the liver (such as autoimmune hepatitis, primary biliary cirrhosis, alcoholic liver disease, sclerosing cholangitis, and autoimmune cholangitis), diabetes (type I or II) and/or the complications thereof, chronic heart failure, congestive heart failure, ischemic diseases (such as stroke and ischemia-reperfusion injury), and myocardial infarction and/or the complications thereof.

It is believed that the compounds of the invention are especially useful for the treatment or prevention of vasculitis, including, but not limited to, giant cell arteritis, Takayasu's arteritis, Polyarteritis nodosa, Kawasaki disease, Wegener's granulomatosis, Churg-Strauss syndrome, microscopic polyangiitis, Henoch-Schönlein purpura, cryoglobulinemia, cutaneous leukocytoclastic angiitis and primary angiitis of the central nervous system.

The invention thus includes the use of said compounds in the manufacture of a medicament for the treatment or prevention of the above-mentioned conditions and diseases. The invention also includes methods for treatment or prevention of such conditions and diseases, comprising administering to a mammal, including man, in need of such treatment an effective amount of a compound as defined above.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic is measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabeling/assay techniques, blotting/chemiluminescence methods, real-time PCR, and the like.

DEFINITIONS

The following definitions shall apply throughout the specification and the appended claims.

Unless otherwise stated or indicated, the term "$C_{1-6}$-alkyl" denotes a straight or branched alkyl group having from 1 to 6 carbon atoms. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc. Examples of said "$C_{1-6}$-alkyl" include methyl, ethyl, n-propyl, isopropyl, n-butyl, isobutyl, sec-butyl, t-butyl and straight- and branched-chain pentyl and hexyl.

Unless otherwise stated or indicated, the term "halo-$C_{1-6}$-alkyl" denotes a straight or branched $C_{1-6}$-alkyl group substituted by one or more halogen atoms. Examples of said halo-$C_{1-6}$-alkyl include 2-fluoroethyl, fluoromethyl, trifluoromethyl and 2,2,2-trifluoroethyl.

Unless otherwise stated or indicated, the term "hydroxy-$C_{1-6}$-alkyl" denotes a straight or branched $C_{1-6}$-alkyl group that has a hydrogen atom thereof replaced with OH. Examples of said hydroxy-$C_{1-6}$-alkyl include hydroxymethyl, 2-hydroxyethyl, 2-hydroxypropyl and 2-hydroxy-2-methylpropyl.

Unless otherwise stated or indicated, the term "cyano-$C_{1-6}$-alkyl" denotes a straight or branched $C_{1-6}$-alkyl group that has a hydrogen atom thereof replaced with cyano. Examples of said cyano-$C_{1-6}$-alkyl include cyanomethyl, 2-cyanoethyl, 2-cyanopropyl and 2-cyano-2-methylpropyl.

The derived expression "$C_{1-6}$-alkoxy" is to be construed accordingly where a $C_{1-6}$-alkyl group is attached to the remainder of the molecule through an oxygen atom. For parts of the range "$C_{1-6}$-alkoxy" all subgroups thereof are contemplated such as $C_{1-5}$-alkoxy, $C_{1-4}$-alkoxy, $C_{1-3}$-alkoxy, $C_{1-2}$-alkoxy, $C_{2-6}$-alkoxy, $C_{2-5}$-alkoxy, $C_{2-4}$-alkoxy, $C_{2-3}$-alkoxy, $C_{3-6}$-alkoxy, $C_{4-5}$-alkoxy, etc. Examples of said "$C_{1-6}$-alkoxy" include methoxy, ethoxy, n-propoxy, isopropoxy, n-butoxy, isobutoxy, sec-butoxy, t-butoxy and straight- and branched-chain pentoxy and hexoxy etc.

Unless otherwise stated or indicated, the term "$C_{1-6}$-alkoxy-$C_{1-6}$-alkyl" refers to a $C_{1-6}$-alkoxy group that is bonded to a $C_{1-6}$-alkyl group via an oxygen atom of said $C_{1-6}$-alkoxy group. Representative examples of such groups include methoxymethyl and ethoxyethyl. Unless otherwise stated or indicated, the term "$C_{1-6}$-acyl" denotes a carbonyl group that is attached through its carbon atom to a hydrogen atom (i.e., a formyl group) or to a straight or branched $C_{1-5}$-alkyl group, where alkyl is defined as above. For parts of the range "$C_{1-6}$-acyl" all subgroups thereof are contemplated such as $C_{1-5}$-acyl, $C_{1-4}$-acyl, $C_{1-3}$-acyl, $C_{1-2}$-acyl, $C_{2-6}$-acyl, $C_{2-5}$-acyl, $C_{2-4}$-acyl, $C_{2-3}$-acyl, $C_{3-6}$-acyl, $C_{4-5}$-acyl, etc. Exemplary acyl groups include formyl, acetyl, propanoyl, butanoyl, pentanoyl, hexanoyl.

Unless otherwise stated or indicated, the term "$C_{1-6}$-alkylsulfonyl" refers to a straight or branched $C_{1-6}$-alkyl group that is bonded to a sulfonyl group. Examples of $C_{1-6}$-alkylsulfonyl groups include methylsulfonyl and ethylsulfonyl.

Unless otherwise stated or indicated, the term "heterocyclyl" or "heterocyclic ring" refers to a fully saturated or partially unsaturated, preferably fully saturated, monocyclic ring system having 4 to 7 ring atoms with at least one heteroatom such as O, N, or S, and the remaining ring atoms are carbon. Examples of heterocyclic rings include piperidinyl, tetrahydropyranyl, tetrahydrofuranyl, tetrahydrothienyl, azepinyl, azetidinyl, oxetanyl, thietanyl, pyrrolidinyl, morpholinyl, imidazolinyl, imidazolidinyl, thiomorpholinyl, pyranyl, dioxanyl, piperazinyl, homopiperazinyl and 5,6-dihydro-4H-1,3-oxazin-2-yl. When present, the sulfur atom may be in an oxidized form (i.e., S=O or O=S=O). Exemplary heterocyclic groups containing sulfur in oxidized form are 1,1-dioxido-thiomorpholinyl and 1,1-dioxido-isothiazolidinyl.

"Halogen" refers to fluorine, chlorine, bromine or iodine.

"Hydroxy" refers to the —OH radical.

"Cyano" refers to the —CN radical.

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

"Prodrugs" refers to compounds that may be converted under physiological conditions or by solvolysis to a biologically active compound of the invention. A prodrug may be inactive when administered to a subject in need thereof, but is converted in vivo to an active compound of the invention. Prodrugs are typically rapidly transformed in vivo to yield the parent compound of the invention, e.g. by hydrolysis in the blood. The prodrug compound usually offers advantages of solubility, tissue compatibility or delayed release in a mammalian organism (see Silverman, R. B., *The Organic Chemistry of Drug Design and Drug Action*, 2$^{nd}$ Ed., Elsevier Academic Press (2004), pp. 498-549). Prodrugs of a compound of the invention may be prepared by modifying functional groups, such as a hydroxy, amino or mercapto groups, present in a compound of the invention in such a way that the modifications are cleaved, either in routine manipulation or in vivo, to the parent compound of the invention. Examples of prodrugs include, but are not limited to, acetate, formate and succinate derivatives of hydroxy functional groups or phenyl carbamate derivatives of amino functional groups.

Throughout the specification and the appended claims, a given chemical formula or name shall also encompass all salts, hydrates, solvates, N-oxides and prodrug forms thereof. Further, a given chemical formula or name shall encompass all tautomeric and stereoisomeric forms thereof. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of formula (I) may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

Compositions

For clinical use, the compounds of the invention are formulated into pharmaceutical formulations for various modes of administration. It will be appreciated that compounds of the invention may be administered together with a physiologically acceptable carrier, excipient, or diluent. The pharmaceutical compositions of the invention may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration. Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the invention may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the is severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Preparation of Compounds of the Invention

The compounds of formula (I) above may be prepared by, or in analogy with, conventional methods. The preparation of intermediates and compounds according to the examples of the present invention may in particular be illuminated by the following Scheme. Definitions of variables in the structures in schemes herein are commensurate with those of corresponding positions in the formulae delineated herein.

Scheme 1

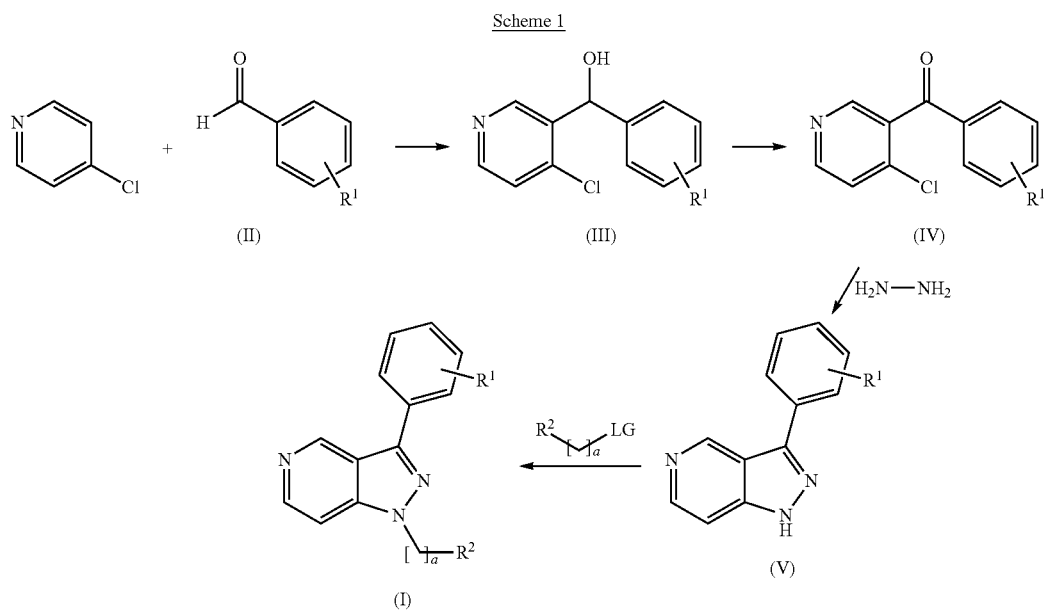

wherein
LG is a leaving group; and
$R^1$, $R^2$ and a are as defined in formula (I).

Compounds of formula (I) may easily be synthesised by hydroxyalkylation of 4-chloropyridine with the appropriate benzaldehyde (II) to give an aryl-(4-chloro-pyridin-3-yl)-methanol derivative (III). Subsequent oxidation of the alcohol results in the corresponding aryl-(4-chloro-pyridin-3-yl)-methanone derivative (IV). Formation of the pyrazolo[4,3-c]pyridine ring system is accomplished by condensation of (IV) with hydrazine to give the 3-aryl-pyrazolo[4,3-c]pyridine intermediate (V). In the last step, the intermediate (V) is alkylated to install the appropriate heterocyclyl or heterocyclyl-alkyl group in the compound of formula (I). A compound of formula (I) can optionally be transformed into another compound of formula (I).

The necessary starting materials for preparing the compounds of formula (I) are either commercially available, or may be prepared by methods known in the art.

The processes described below in the experimental section may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are mentioned above.

The compounds of formula (I) may possess one or more chiral carbon atoms, and they may therefore be obtained in the form of optical isomers, e.g., as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes delineated herein may include, for example, solvents, reagents, catalysts, and protecting group and deprotecting group reagents.

Examples of protecting groups are t-butoxycarbonyl (Boc), benzyl and trityl (triphenylmethyl). The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The following abbreviations have been used:

| | |
|---|---|
| Ac | Acetate |
| Aq | Aqueous |
| Boc | tert-Butoxycarbonyl |
| Calcd | Calculated |
| Cbz | Carboxybenzyloxy |
| d | Day |
| DCM | Dichloromethane |
| DIAD | Diisopropyl azodicarboxylate |
| DIPEA | Diisopropylethylamine |
| DMF | N,N'-Dimethylformamide |
| ES+ | Electrospray |
| h | Hour(s) |
| HPLC | High performance liquid chromatography |
| HRMS | High resolution mass spectrometry |
| IR | Infrared |
| LCMS | Liquid chromatography mass spectrometry |
| M | Molar |
| [MH+] | Protonated molecular ion |

| | |
|---|---|
| min | Minutes |
| NMR | Nuclear Magnetic resonance |
| RP | Reverse phase |
| $R_T$ | Retention time |
| MS | Mass spectrometry |
| sat | Saturated |
| sec | Seconds |
| THF | Tetrahydrofuran |
| TFA | Trifluoroacetic acid |
| TMS | Tetramethylsilane |

The recitation of a listing of chemical groups in any definition of a variable herein includes definitions of that variable as any single group or combination of listed groups. The recitation of an embodiment herein includes that embodiment as any single embodiment or in combination with any other embodiments or portions thereof.

The invention will now be further illustrated by the following non-limiting examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent. All references and publications cited herein are hereby incorporated by reference in their entirety.

EXAMPLES AND INTERMEDIATE COMPOUNDS

Experimental Methods

All reagents were commercial grade and were used as received without further purification, unless otherwise specified. Reagent grade solvents were used in all cases. Analytical LCMS was performed on a Waters ZQ mass spectrometer connected to an Agilent 1100 HPLC system. Analytical HPLC was performed on an Agilent 1100 system. High-resolution mass spectra (HRMS) were obtained on an Agilent MSD-TOF connected ici to an Agilent 1100 HPLC system. During the analyses the calibration was checked by two masses and automatically corrected when needed. Spectra are acquired in positive electrospray mode. The acquired mass range was m/z 100-1100. Profile detection of the mass peaks was used. Flash chromatography was performed on either a Flash Master Personal system equipped with Strata SI-1 silica gigatubes or by gravity flash is chromatography using Apollo Scientific silica gel (40-63 μm, 60 Å). Reverse Phase HPLC was performed on a Gilson system (Gilson 322 pump with Gilson 321 equilibration pump and Gilson 215 autosampler) equipped with YMC ODS-A 100/150×20 mm columns. Preparative LCMS was performed on a Waters system (2× Gemini, X18, 110 Å, 50×21.2 mm, 5 μm). Microwave irradiations were carried out using a Biotage microwave. The compounds were automatically named using ACD 6.0.

Analytical HPLC and LCMS data were obtained with:

System A: Phenomenex Synergi Hydro RP (C18, 30×4.6 mm, 4 nm), gradient 5-100% $CH_3CN$ (+0.085% TFA) in water (+0.1% TFA), 1.5 mL/min, gradient time 1.75 min, 200 nm, 30° C.; or System B: Phenomenex Synergi Hydro RP (C18, 150×4.6 mm, 4 nm), gradient 5-100% $CH_3CN$ (+0.085% TFA) in water (+0.1% TFA), 1.5 mL/min, gradient time 7 min, 200 nm, 30° C.; or System C: Phenomenex Synergi Hydro RP-80A (C18, 150×4.6 mm, 4 nm), gradient 5-95% $CH_3CN$ (+0.1% $HCO_2H$) in water (+0.1% $HCO_2H$), 1 mL/min, gradient time 15.5 min, 200-300 nm, 40° C.

Intermediate 1

3-(4-Chlorophenyl)-1H-pyrazolo[4,3-c]pyridine

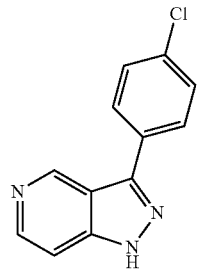 [SMILES: Clc1ccc(-c2n[nH]c3ccncc23)cc1]

Diisopropylamine (11.7 mL, 83.3 mmol) was dissolved in THF (200 mL) under a nitrogen atmosphere at 0° C. and n-butyllithium (52.5 mL, 1.6 M in hexanes, 84.0 mmol) was added. The solution was stirred for 1 h, cooled to −78° C. and 4-chloropyridine hydrochloride (5.00 g, 33.3 mmol) was added portionwise. The reaction mixture was stirred 2 h and 4-chlorobenzaldehyde (4.68 g, 33.3 mmol) was added. The reaction mixture was allowed to warm slowly to room temperature and stirred for 3 d. Sat aq $NH_4Cl$ solution (20 mL) was iii added and the reaction mixture was poured into 1 M aq $Na_2CO_3$ solution (500 mL). The layers were separated and the aq layer was extracted with DCM (2×500 mL). The combined organic layers were dried ($MgSO_4$) and the solvents were removed in vacuo to give (4-chlorophenyl)-(4-chloro-pyridin-3-yl)-methanol (7.57 g, 89.4%) as a light brown solid.

Analytical HPLC: purity 77% (System B, $R_T$=4.55 min); Analytical LCMS: purity>90% (System A, $R_T$=1.66 min), ES$^+$: 254.0 [$^{35}$ClMH]$^+$ and 256.0 [$^{37}$ClMH]$^+$.

(4-Chlorophenyl)-(4-chloro-pyridin-3-yl)-methanol (7.57 g, 29.8 mmol) was dissolved in dry acetone (150 mL) and chromium (VI) oxide (8.94 g, 89.4 mmol) was added. The reaction mixture was stirred for 18 h and then poured into sat aq $NaHCO_3$ solution (500 mL) and extracted with DCM (2×500 mL). The combined organic layers were dried ($MgSO_4$) and the solvents were removed in vacuo. The residue was purified by column chromatography (normal phase, 50 g, Strata SI-1, silica gigatube, DCM (600 mL)) to give (4-chlorophenyl)-(4-chloropyridin-3-yl)-methanone (4.88 g, 65.0%) as a yellow oil.

Analytical LCMS: purity 100% (System A, $R_T$=2.14 min), ES$^+$: 252.0 [$^{35}$ClMH]$^+$ and 254.0 [$^{37}$ClMH]$^+$.

(4-Chlorophenyl)-(4-chloropyridin-3-yl)-methanone (3.88 g, 15.4 mmol) was dissolved in MeOH (20 mL) at room temperature and hydrazine hydrate (20 mL) was added. The reaction mixture was stirred for 3 h. The precipitate was filtered and purified by recrystallisation from PhMe/MeOH (~4:1, ~150 mL) to give 3-(4-chlorophenyl)-1H-pyrazolo[4, 3-c]pyridine (1.16 g, 33.0%) as a yellow solid.

Analytical HPLC: purity 99.2% (System B, $R_T$=4.29 min); Analytical LCMS: purity 94.8% (System B, $R_T$=4.69 min), ES$^+$: 230.0 [$^{35}$ClMH]$^+$ and 232.1 [$^{37}$ClMH]$^+$.

Intermediate 2

3-(4-Fluorophenyl)-1H-pyrazolo[4,3-c]pyridine

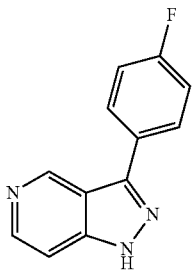 [SMILES: Fc1ccc(-c2n[nH]c3ccncc23)cc1]

3-(4-Fluorophenyl)-1H-pyrazolo[4,3-c]pyridine was prepared according to the method to used for the preparation of Intermediate 1, but using 4-fluorobenzaldehyde instead of 4-chlorobenzaldehyde. Excess MnO$_2$ was used instead of CrO$_3$ in the oxidation step. The title compound was obtained as a yellow solid (791 mg, 55.8% overall yield, 3 steps).

Analytical HPLC: purity 95.3% (System B, $R_T$=3.97 min); Analytical LCMS: purity>90% (System A, $R_T$=1.38 min), ES$^+$: 214.4 [MH]$^+$.

Intermediate 3

3-(4-Methylphenyl)-1H-pyrazolo[4,3-c]pyridine

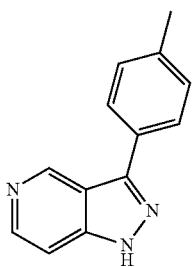 [SMILES: Cc1ccc(-c2n[nH]c3ccncc23)cc1]

3-(4-Methylphenyl)-1H-pyrazolo[4,3-c]pyridine was prepared according to the method used for the preparation of Intermediate 1, but using 4-methylbenzaldehyde instead of 4-chlorobenzaldehyde. Excess MnO$_2$ was used instead of CrO$_3$ in the oxidation step. The title compound was obtained as an off-white solid (2.05 g, 16% overall yield, 3 steps).

Analytical LCMS: purity 100% (System C, $R_T$=3.26 min), ES$^+$: 210 [MH]$^+$.

Intermediate 4

4-(1H-Pyrazolo[4,3-c]pyridin-3-yl)-benzonitrile

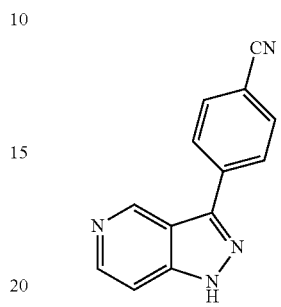

4-(1H-Pyrazolo[4,3-c]pyridin-3-yl)-benzonitrile was prepared according to the method used for the preparation of Intermediate 1, but using 4-formyl-benzonitrile instead of 4-chlorobenzaldehyde. The title compound was obtained as a white solid (846 mg, 28.8% overall yield, 3 steps).

Analytical HPLC: purity 95.8% (System B, $R_T$=3.76 min); Analytical LCMS: purity>90% (System A, $R_T$=1.38 min), ES$^+$: 221.4 [MH]$^+$.

Example 1

3-(4-Fluorophenyl)-1-(tetrahydro-2H-pyran-4-yl)-1H-pyrazolo[4,3-c]pyridine

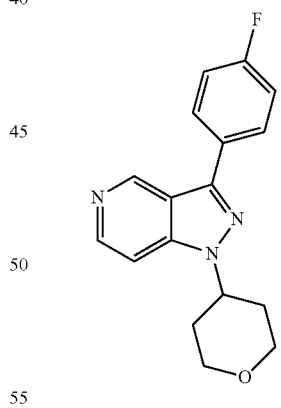

Intermediate 2 (200 mg, 0.94 mmol) and triphenylphosphine (369 mg, 1.41 mmol) were is suspended in DCM (5 mL) and 4-hydroxytetrahydropyran (134 µL, 1.41 mmol) was added, followed by DIAD (277 µL, 1.41 mmol). The reaction mixture was stirred for 3 d. The solvent was removed in vacuo to give a yellow gum. The residue was purified by reverse phase HPLC (YMC ODS-A 100×20 mm, 5 µm, 25 mL/min, gradient 60% to 100% (over 7 min) then 100% (3 min) MeOH in 10% MeOH/water) to give 3-(4-fluorophenyl)-1-(tetrahydro-2H-pyran-4-yl)-1H-pyrazolo[4,3-c]pyridine (29 mg, 10.4%) as a white solid.

Analytical HPLC: purity 99.6% (System B, $R_T$=4.67 min); Analytical LCMS: purity 100% (System B, $R_T$=4.61 min), ES$^+$: 298.5 [MH]$^+$; HRMS calcd for $C_{17}H_{16}FN_3O$: 297.1277. found 297.1284.

Example 2

3-(4-Chlorophenyl)-2-(tetrahydro-2H-pyran-4-yl)-2H-pyrazolo[4,3-c]pyridine

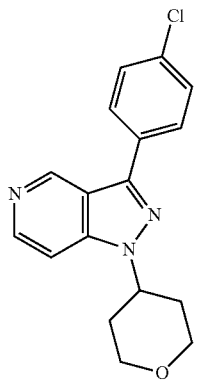 [SMILES: Clc1ccc(-c2nn(C3CCOCC3)c3ccncc23)cc1]

Intermediate 1 (100 mg, 0.44 mmol) and triphenylphosphine (129 mg, 0.49 mmol) were suspended in DCM (2 mL) and 4-hydroxytetrahydropyran (43.0 µL, 0.45 mmol) and DIAD (97.0 µL, 0.49 mmol) were added. The reaction mixture was stirred for 5 d. The solvents were removed in vacuo and the residue was purified by reverse phase HPLC (YMC ODS-A 100×20 mm, 5 µm, 25 mL/min, gradient 40% to 100% (over 7 min) then 100% (3 min) MeOH in 10% MeOH/water) to give 3-(4-chlorophenyl)-2-(tetrahydro-2H-pyran-4-yl)-2H-pyrazolo[4,3-c]pyridine (11 mg, 7.8%) as a white solid.

Analytical HPLC: purity 99.5% (System B, $R_T$=4.97 min); Analytical LCMS: purity 100% (System B, $R_T$=5.34 min), ES$^+$: 314.0 [$^{35}$ClMH]$^+$ and 316.0 [$^{37}$ClMH]$^+$; HRMS calcd for $C_{17}H_{16}ClN_3O$: 313.0982. found 313.0980.

Example 3

3-(4-Methylphenyl)-1-(tetrahydro-2H-pyran-4-yl)-1H-pyrazolo[4,3-c]pyridine

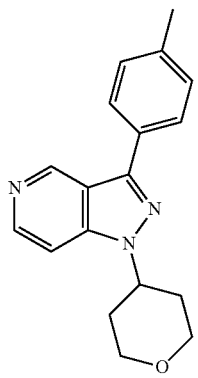 [SMILES: Cc1ccc(-c2nn(C3CCOCC3)c3ccncc23)cc1]

4-Hydroxytetrahydropyran (4.86 g, 47.6 mmol) was dissolved in DCM (40 mL) and triethylamine (6.95 mL, 49.9 mmol). The reaction mixture was cooled to 0° C. and a solution of methanesulfonyl chloride (5.72 g, 49.9 mmol) in DCM (10 mL) was added dropwise. The reaction mixture was stirred at 0° C. for 5 min and then allowed to warm to room temperature and stirred for 20 h. The solvents were removed in vacuo to give a white residue which was partitioned between EtOAc and H$_2$O. The aq phase was extracted with EtOAc (2×100 mL). The organic layers were combined, dried (MgSO$_4$) and the solvents were removed in vacuo to give tetrahydro-2H-pyran-4-yl methanesulfonate (8.53 g, 99%) as a colourless gum which solidified on standing.

Intermediate 3 (0.40 g, 1.91 mmol), tetrahydro-2H-pyran-4-yl methanesulfonate (1.03 g, 5.72 mmol) and K$_2$CO$_3$ (0.52 g, 3.76 mmol) were dissolved in MeCN (7 mL) and the reaction mixture was heated under reflux for 50 h. The solvents were removed in vacuo. The resulting residue was partitioned between EtOAc (25 mL) and H$_2$O (25 mL). The aqueous phase was extracted with EtOAc (2×100 mL). The organic layers were combined, dried (MgSO$_4$) and the solvents were removed in vacuo. The residue was purified by Waters Preparative LC-MS (2× Gemini, X18, 110 Å, 50×21.2 mm, 5 µm, 20 mL/min, 25° C., gradient 5% (held for 0.6 min) to 100% (over 10 min), MeCN in H$_2$O (0.1% formic acid), 200-800 nm) to give 3-(4-methylphenyl)-1-(tetrahydro-2H-pyran-4-yl)-1H-pyrazolo[4,3-c]pyridine (103 mg, 18.6%) as an off-white solid.

Analytical HPLC: purity 99.0% (System B, $R_T$=9.02 min); Analytical LCMS: purity 100% (System B, $R_T$=8.39 min), ES$^+$: 294.6 [MH]$^+$; HRMS calcd for $C_{18}H_{19}N_3O$: 293.1528. found 293.1528.

Example 4

3-(4-Chlorophenyl)-1-[(3R)-tetrahydrofuran-3-yl]-1H-pyrazolo[4,3-c]pyridine

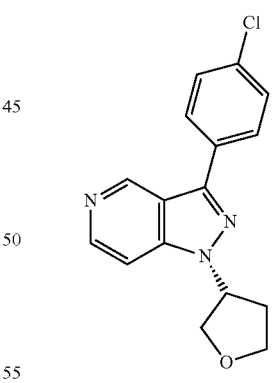

Intermediate 1 (200 mg, 0.87 mmol) and triphenylphosphine (342 mg, 1.31 mmol) were suspended in DCM (5 mL) and (S)-3-hydroxy-tetrahydrofuran (89.0 µL, 1.31 mmol) was added, followed by DIAD (257 µL, 1.31 mmol). The reaction mixture was stirred at room temperature for 48 h. The solvents were removed in vacuo. The residue was purified by reverse phase HPLC (YMC ODS-A 100×20 mm, 5 µm, 25 mL/min, gradient 60% to 100% (over 7 min) then 100% (3 min) MeOH in 10% MeOH/water) to give 3-(4-chlorophenyl)-1-[(3R)-tetrahydro furan-3-yl]-1H-pyrazolo[4,3-c]pyridine (153 mg, 58.6%) as a light yellow gum.

Analytical HPLC: purity 100% (System B, $R_T$=4.78 min); Analytical LCMS: purity 100% (System B, $R_T$=4.88 min), ES$^+$: 300.5 [$^{35}$ClMH]$^+$ and 302.5 [$^{37}$ClMH]$^+$; HRMS calcd for $C_{16}H_{14}ClN_3O$: 299.0825. found 299.0831.

Example 5

3-(4-Chlorophenyl)-1-piperidin-4-yl-1H-pyrazolo[4,3-c]pyridine

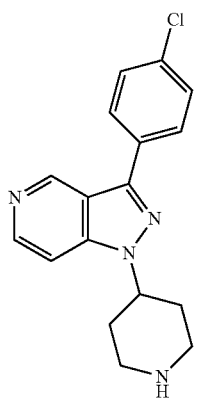 [SMILES: Clc1ccc(-c2nn(C3CCNCC3)c3ccncc23)cc1]

Polymer-bound triphenylphosphine (1.81 g, 3 mmol/g, 5.44 mmol) was suspended in DCM (10 mL) and stirred for 30 min. DIAD (1.07 mL, 5.44 mmol), 1-Boc-4-hydroxypiperidine (1.09 g, 5.44 mmol) and Intermediate 1 (500 mg, 2.18 mmol) were added. The reaction mixture was stirred at room temperature for 18 h. The reaction mixture was filtered and the filtrate concentrated in vacuo. The residue was purified by reverse phase HPLC (YMC ODS-A 100×20 mm, 5 μm, 25 mL/min, gradient 40% to 100% (over 7 min) then 100% (3 min) MeOH in 10% MeOH/water) to give 4-[3-(4-chlorophenyl)-pyrazolo[4,3-c]pyridin-1-yl]-piperidine-1-carboxylic acid tert-butyl ester (200 mg, 22.2%) as a light yellow gum.

Analytical HPLC: purity 100% (System B, $R_T$=6.13 min); Analytical LCMS: purity>90% (System A, $R_T$=2.09 min), ES$^+$: 412.9 [$^{35}$ClMH]$^+$ and 415.0 [$^{37}$ClMH]$^+$.

4-[3-(4-Chlorophenyl)-pyrazolo[4,3-c]pyridin-1-yl]-piperidine-1-carboxylic acid tert-butyl ester (200 mg, 0.48 mmol) was dissolved in DCM (5 mL) and TFA (5 mL) was added. The reaction mixture was stirred at room temperature for 30 min. The solvents were removed in vacuo and the residue was dissolved in 1 M aq $Na_2CO_3$ solution (50 mL) and extracted with DCM (3×50 mL). The combined organic layers were dried (MgSO$_4$) and the solvents removed in vacuo. The residue was purified by reverse phase HPLC (YMC ODS-A 100×20 mm, 5 μm, 25 mL/min, gradient 40% to 100% (over 7 min) then 100% (3 min) MeOH in 10% MeOH/water) to give 3-(4-chlorophenyl)-1-piperidin-4-yl-1H-pyrazolo[4,3-c]-pyridine (76 mg, 50.2%) as a white solid.

Analytical HPLC: purity 100% (System B, $R_T$=3.74 min); Analytical LCMS: purity 100% (System B, $R_T$=3.60 min), ES$^+$: 313.1 [$^{35}$ClMH]$^+$ and 315.0 [$^{37}$ClMH]$^+$; HRMS calcd for $C_{17}H_{17}ClN_4$: 312.1142. found 312.1141.

Example 6

3-(4-Chlorophenyl)-1-(1-methylpiperidin-4-yl)-1H-pyrazolo[4,3-c]pyridine

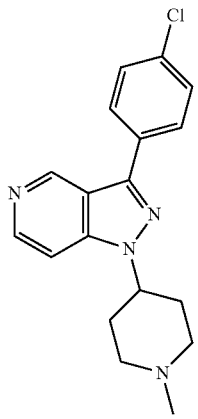 [SMILES: CN1CCC(n2nc(-c3ccc(Cl)cc3)c3cnccc32)CC1]

Polymer-bound triphenylphosphine (670 mg, 3 mmol/g, 2.00 mmol) was suspended in DCM (5 mL) and stirred for 30 min. DIAD (396 μL, 2.01 mmol), 4-hydroxy-N-methyl-piperidine (232 mg, 2.01 mmol) and Intermediate 1 (185 mg, 0.81 mmol) were added. The reaction mixture was stirred for 18 h. The reaction mixture was filtered and the filtrate concentrated in vacuo. The residue was purified by reverse phase HPLC (YMC ODS-A 100×20 mm, 5 μm, 25 mL/min, gradient 60% to 100% (over 7 min) then 100% (3 min) MeOH in 10% MeOH/water), then by reverse phase HPLC (YMC ODS-A 150×20 mm, 5 μm, 15 mL/min, gradient 0% to 40% (over 12 min) then 100% (3 min) MeOH in water (1% formic acid)). The residue was de-salted using $K_2CO_3$ in DCM to give 3-(4-chlorophenyl)-1-(1-methylpiperidin-4-yl)-1H-pyrazolo[4,3-c]pyridine (31 mg, 11.8%) as a white solid.

Analytical HPLC: purity 100% (System B, $R_T$=3.77 min); Analytical LCMS: purity 100% (System B, $R_T$=4.16 min), ES$^+$: 327.0 [$^{35}$ClMH]$^+$ and 329.0 [$^{37}$ClMH]$^+$; HRMS calcd for $C_{18}H_{19}ClN_4$: 326.1298. found 326.1303.

Example 7

{4-[3-(4-Chlorophenyl)-1H-pyrazolo[4,3-c]pyridin-1-yl]piperidin-1-yl}acetonitrile

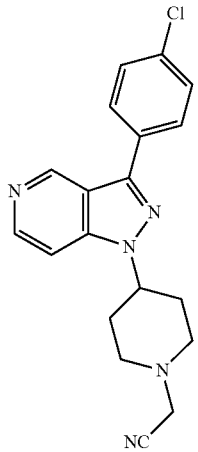 [SMILES: N#CCN1CCC(n2nc(-c3ccc(Cl)cc3)c3cnccc32)CC1]

Example 5 (185 mg, 0.59 mmol) was dissolved in DMF (5 mL) and DIPEA (91.6 mg, 123 µL, 0.71 mmol) and iodoacetonitrile (51.0 µL, 0.71 mmol) were added. The reaction mixture was heated using a Biotage microwave (100° C., absorption high, pre-stirring 30 sec) for 10 min, and then concentrated in vacuo. The residue was dissolved in MeOH (5 mL), poured into 1 M aq $Na_2CO_3$ solution (50 mL) and extracted with EtOAc (3×50 mL). The combined organic layers were dried ($MgSO_4$) and concentrated in vacuo. The residue was purified by reverse phase HPLC (YMC ODS-A 100×20 mm, 5 µm, 25 mL/min, gradient 60% to 100% (over 7 min) then 100% (3 min) MeOH in 10% MeOH/water) to give {4-[3-(4-chlorophenyl)-1H-pyrazolo[4,3-c]pyridin-1-yl]piperidin-1-yl}acetonitrile (86 mg, 41.4%) as a cream solid.

Analytical HPLC: purity 97.9% (System B, $R_T$=4.57 min); Analytical LCMS: purity 100% (System B, $R_T$=4.61 min), ES$^+$: 352.5 [$^{35}$ClMH]$^+$ and 354.5 [$^{37}$ClMH]$^+$; HRMS calcd for $C_{19}H_{18}ClN_5$: 351.1251. found 351.1246

Example 8

3-(4-Chlorophenyl)-1-(tetrahydro-2H-pyran-4-ylmethyl)-1H-pyrazolo[4,3-c]pyridine

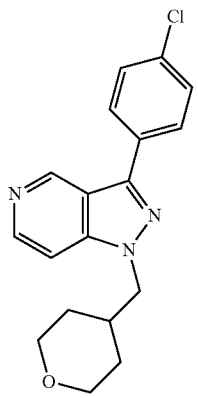 [SMILES: Clc1ccc(-c2nn(CC3CCOCC3)c3ccncc23)cc1]

Sodium hydride (52 mg, 60% dispersion in mineral oil, 1.31 mmol) was suspended in THF (3 mL) and Intermediate 1 (200 mg, 0.87 mmol) and 4-bromomethyltetrahydropyran (187 mg, 1.04 mmol) were added. The reaction mixture was heated using a Biotage microwave (100° C., absorption normal, pre-stirring 15 sec) for 1 h, then at 120° C. for 1 h and at 125° C. for 30 min, and then concentrated in vacuo. The residue was poured into 1 M aq $Na_2CO_3$ solution (50 mL) and extracted with DCM (3×50 mL). The combined organic layers were dried ($MgSO_4$) and concentrated in vacuo. The residue was purified by reverse phase HPLC (YMC ODS-A 100×20 mm, 5 µm, 25 mL/min, gradient 60% to 100% (over 7 min) then 100% (3 min) MeOH in 10% MeOH/water and YMC ODS-A 150×20 mm, 5 µm, 15 mL/min, gradient 4% to 100% (over 12 min) then 100% (3 min) MeOH+1% formic acid in water+1% formic acid). The residue was de-salted using $K_2CO_3$ in DCM to give 3-(4-chlorophenyl)-1-(tetrahydro-2H-pyran-4-ylmethyl)-1H-pyrazolo[4,3-c]pyridine as a yellow gum (106 mg, 0.33 mmol, 37.1%).

Analytical HPLC: purity 100% (System B, $R_T$=4.99 min); Analytical LCMS: purity 100% is (System B, $R_T$=5.38 min), ES$^+$: 328.0 [$^{35}$ClMH]$^+$ and 330.0 [$^{37}$ClMH]$^+$; HRMS calcd for $C_{18}H_{18}ClN_3O$: 327.1138. found 327.1149.

Example 9

3-(4-Chlorophenyl)-1-[1-(methylsulfonyl)piperidin-4-yl]-1H-pyrazolo[4,3-c]pyridine

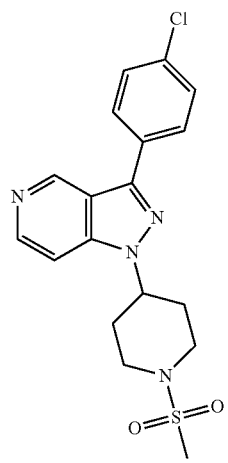 [SMILES: CS(=O)(=O)N1CCC(n2nc(-c3ccc(Cl)cc3)c3cnccc32)CC1]

Example 5 (123 mg, 0.39 mmol) was dissolved in DCM (5 mL) and DIPEA (75 µL, 0.43 mmol) and methanesulfonyl chloride (33.5 µL, 0.43 mmol) were added. The reaction mixture was stirred for 2 h, diluted with DCM (50 mL), washed with 1 M aq $Na_2CO_3$ solution (50 mL) and the organic layer was dried ($MgSO_4$) and concentrated in vacuo. The residue was purified by reverse phase HPLC (YMC ODS-A 100×20 mm, 5 µm, 25 mL/min, gradient 40% to 100% (over 7 min) then 100% (3 min) MeOH in 10% MeOH/water) to give 3-(4-chlorophenyl)-1-[1-(methylsulfonyl)piperidin-4-yl]-1H-pyrazolo[4,3-c]pyridine (61 mg, 39.7%) as a white solid.

Analytical HPLC: purity 100% (System B, $R_T$=4.98 min); Analytical LCMS: purity 100% (System B, $R_T$=5.03 min), ES$^+$: 391.5 [$^{35}$ClMH]$^+$ and 393.6 [$^{37}$ClMH]$^+$; HRMS calcd for $C_{18}H_{19}ClN_4O_2S$: 390.0917. found 390.0926.

Example 10

1-(1-Acetylpiperidin-4-yl)-3-(4-chlorophenyl)-1H-pyrazolo[4,3-c]pyridine

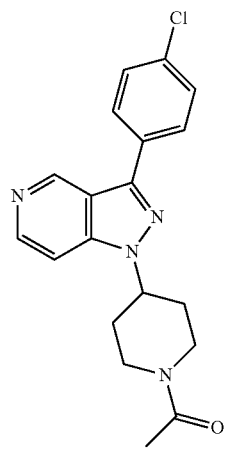 [SMILES: CC(=O)N1CCC(n2nc(-c3ccc(Cl)cc3)c3cnccc32)CC1]

Example 5 (167 mg, 0.53 mmol) was dissolved in DCM (5 mL) and DIPEA (102 μL, 0.59 mmol) and acetyl chloride (41.5 μL, 0.59 mmol) were added. The reaction mixture was stirred for 2 h, diluted with DCM (50 mL), washed with 1 M aq $Na_2CO_3$ solution (50 mL) and the organic layer was dried ($MgSO_4$) and concentrated in vacuo. The residue was purified by reverse phase HPLC (YMC ODS-A 100×20 mm, 5 μm, 25 mL/min, gradient 60% to 100% (over 7 min) then 100% (3 min) MeOH in 10% MeOH/water), dissolved in EtOAc (50 mL), washed with 1 M aqueous HCl (50 mL), dried ($MgSO_4$) and concentrated in vacuo to give 1-(1-acetylpiperidin-4-yl)-3-(4-chlorophenyl)-1H-pyrazolo[4,3-c]pyridine (35 mg, 18.6%) as a white solid.

Analytical HPLC: purity 100% (System B, $R_T$=4.62 min); Analytical LCMS: purity 100% (System B, $R_T$=4.70 min), $ES^+$: 355.6 $[^{35}ClMH]^+$ and 357.5 $[^{37}ClMH]^+$; HRMS calcd for $C_{19}H_{19}ClN_4O$: 354.1247. found 354.1263.

Example 11

3-(4-Chlorophenyl)-1-[1-(2-methoxyethyl)piperidin-4-yl]-1H-pyrazolo[4,3-c]pyridine

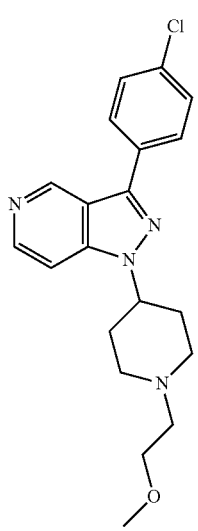 [SMILES: COCCN1CCC(n2nc(-c3ccc(Cl)cc3)c3cnccc32)CC1]

Example 5 (162 mg, 0.52 mmol) was dissolved in DMF (5 mL) and DIPEA (108 μL, 0.62 mmol) and (2-bromoethyl) methyl ether (58 μL, 0.62 mmol) were added. The reaction mixture was heated using a Biotage microwave (100° C., absorption high, pre-stirring 30 sec) for 10 min and at 120° C. for 10 min, and then concentrated in vacuo. The residue was dissolved in MeOH (5 mL), poured into 1 M aq $Na_2CO_3$ solution (50 mL) and extracted with EtOAc (3×50 mL). The combined organic layers were dried ($MgSO_4$) and concentrated in vacuo. The residue was purified by reverse phase HPLC (YMC ODS-A 100×20 mm, 5 μm, 25 mL/min, gradient 60% to 100% (over 7 min) then 100% (3 min) MeOH in 10% MeOH/water and YMC ODS-A 100×20 mm, 5 μm, 25 mL/min, gradient 60% to 90% (over 7 min) then 100% (3 min) MeOH in 10% MeOH/water) to give 3-(4-chlorophenyl)-1-[1-(2-methoxyethyl)piperidin-4-yl]-1H-pyrazolo[4,3-c]pyridine (29 mg, 15.0%) as a colourless gum.

Analytical HPLC: purity 99.8% (System B, $R_T$=3.96 min); Analytical LCMS: purity 100% (System B, $R_T$=4.01 min), $ES^+$: 371.6 $[^{35}ClMH]^+$ and 373.5 $[^{37}ClMH]^+$; HRMS calcd for $C_{20}H_{23}ClN_4O$: 370.1560. found 370.1575.

Example 12

3-(4-Chlorophenyl)-1-piperidin-3-yl-1H-pyrazolo[4,3-c]pyridine

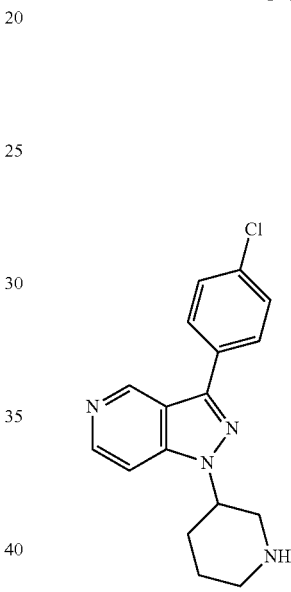

Intermediate 1 (200 mg, 0.87 mmol) and triphenylphosphine (342 mg, 1.31 mmol) were suspended in DCM (5 mL) and 1-Boc-3-hydroxypiperidine (263 mg, 1.31 mmol) and DIAD (257 μL, 1.31 mmol) were added. The reaction mixture was stirred for 3 h and TFA (3 mL) was added. The reaction mixture was stirred for 1 h and concentrated in vacuo. The residue was dissolved in 1 M aq HCl (50 mL) and washed with DCM (2×30 mL). The aq layer was basified with NaOH and extracted with DCM (3×50 mL). The combined organic extracts were dried ($MgSO_4$) and concentrated in vacuo. The residue was purified by reverse phase HPLC (YMC ODS-A 100×20 mm, 5 μm, 25 mL/min, gradient 60% to 100% (over 7 min) then 100% (3 min) MeOH in 10% MeOH/water) to give 3-(4-chlorophenyl)-1-piperidin-3-yl-1H-pyrazolo[4,3-c]pyridine (41 mg, 15.1%) as a white solid.

Analytical HPLC: purity 98.2% (System B, $R_T$=3.85 min); Analytical LCMS: purity 100% (System B, $R_T$=3.86 min), ES⁺: 313.6 [$^{35}$ClMH]⁺ and 315.6 [$^{37}$ClMH]⁺; HRMS calcd for $C_{17}H_{17}ClN_4$: 312.1142. found 312.1152.

Example 13

3-(4-Chlorophenyl)-1-[(3S)-tetrahydrofuran-3-yl]-1H-pyrazolo[4,3-c]pyridine

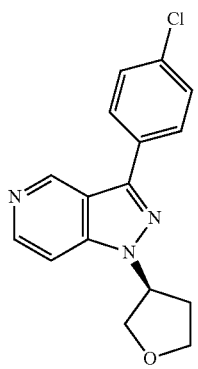 [SMILES: Clc1ccc(-c2nn([C@H]3CCOC3)c3ccncc23)cc1]

Intermediate 1 (200 mg, 0.87 mmol) and triphenylphosphine (342 mg, 1.31 mmol) were suspended in DCM (5 mL) and (R)-3-hydroxy-tetrahydrofuran (89 μL, 1.31 mmol) and DIAD (257 μL, 1.31 mmol) were added. The reaction mixture was stirred for 4 h and concentrated in vacuo. The residue was purified by reverse phase HPLC (YMC ODS-A 100×20 mm, 5 μm, 25 mL/min, gradient 60% to 100% (over 7 min) then 100% (3 min) MeOH in 10% MeOH/water) to give 3-(4-chlorophenyl)-1-[(3S)-tetrahydro furan-3-yl]-1H-pyrazolo[4,3-c]pyridine (160 mg, 61.3%) as a colourless gum.

Analytical HPLC: purity 100% (System B, $R_T$=4.82 min); Analytical LCMS: purity 100% (System B, $R_T$=4.86 min), ES⁺: 300.5 [$^{35}$ClMH]⁺ and 302.5 [$^{37}$ClMH]⁺; HRMS calcd for $C_{16}H_{14}ClN_3O$: 299.0825. found 299.0835.

Example 14

3-(4-Chlorophenyl)-1-(tetrahydrofuran-3-ylmethyl)-1H-pyrazolo[4,3-c]pyridine

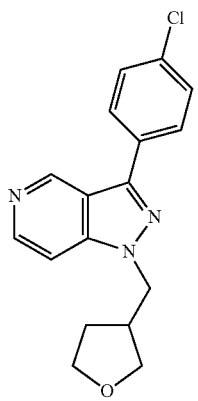 [SMILES: Clc1ccc(-c2nn(CC3CCOC3)c3ccncc23)cc1]

Intermediate 1 (200 mg, 0.87 mmol) and triphenylphosphine (342 mg, 1.31 mmol) were suspended in DCM (5 mL) and tetrahydro-3-furan-methanol (126 μL, 1.31 mmol) and DIAD (257 μL, 1.31 mmol) were added. The reaction mixture was stirred for 3 d and concentrated in vacuo. The residue was purified by reverse phase HPLC (YMC ODS-A 100×20 mm, 5 μm, 25 mL/min, gradient 60% to 100% (over 7 min) then 100% (3 min) MeOH in 10% MeOH/water) to give 3-(4-chlorophenyl)-1-(tetrahydrofuran-3-ylmethyl)-1H-pyrazolo[4,3-c]pyridine (118 mg, 43.2%) as a colourless gum.

Analytical HPLC: purity 99.7% (System B, $R_T$=4.88 min); Analytical LCMS: purity 100% (System B, $R_T$=4.94 min), ES⁺: 314.6 [$^{35}$ClMH]⁺ and 316.5 [$^{37}$ClMH]⁺; HRMS calcd for $C_{17}H_{16}ClN_3O$: 313.0982. found 313.0990.

Example 15

3-(4-Chlorophenyl)-1-(1-ethylpiperidin-4-yl)-1H-pyrazolo[4,3-c]pyridine

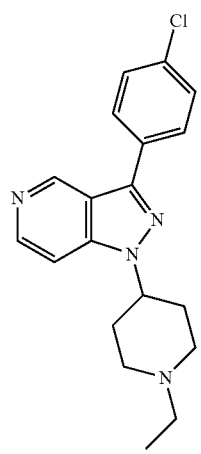 [SMILES: CCN1CCC(n2nc(-c3ccc(Cl)cc3)c3cnccc32)CC1]

Example 5 (162 mg, 0.52 mmol) was dissolved in DMF (5 mL) and DIPEA (99.0 μL, 0.57 mmol) and iodoethane (46 μL, 0.57 mmol) were added. The reaction mixture was stirred for 11 d and concentrated in vacuo. The residue was dissolved in MeOH (5 mL), poured into 1 M aq $Na_2CO_3$ solution (50 mL) and extracted with DCM (2×50 mL). The combined organic layers were dried ($MgSO_4$) and concentrated in vacuo. The residue was purified by reverse phase HPLC (YMC ODS-A 100×20 mm, 5 μm, 25 mL/min, gradient 60% to 100% (over 7 min) then 100% (3 min) MeOH in 10% MeOH/water) to give 3-(4-chlorophenyl)-1-(1-ethylpiperidin-4-yl)-1H-pyrazolo[4,3-c]pyridine (60 mg, 33.9%) as a colourless gum.

Analytical HPLC: purity 97.7% (System B, $R_T$=3.89 min); Analytical LCMS: purity 100% (System B, $R_T$=3.94 min), ES⁺: 341.5 [$^{35}$ClMH]⁺ and 343.4 [$^{37}$ClMH]⁺; HRMS calcd for $C_{19}H_{21}ClN_4$: 340.1455. found 340.1465.

Example 16

3-(4-Chlorophenyl)-1-(1-isopropylpiperidin-4-yl)-1H-pyrazolo[4,3-c]pyridine

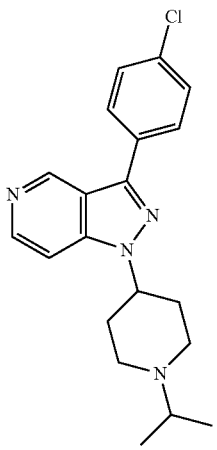 [SMILES: CC(C)N1CCC(n2nc(-c3ccc(Cl)cc3)c3cnccc32)CC1]

Example 5 (257 mg, 0.82 mmol) was dissolved in DCM (10 mL) and acetone (121 µL, 1.64 mmol), 4 Å molecular sieves (560 mg) and AcOH (1 drop) were added. The reaction mixture was stirred for 4 h and NaBH(OAc)$_3$ (184 mg, 1.64 mmol) was added. The reaction mixture was stirred for 16 h. Acetone (200 µL) and NaBH(OAc)$_3$ (200 mg) were added and the reaction mixture was stirred for 4 d. 1 M aq Na$_2$CO$_3$ (2 mL) was added and the reaction mixture was stirred for 1 h, poured into 1 M aq Na$_2$CO$_3$ solution (50 mL) and extracted with DCM (3×50 mL). The combined organic layers were dried (MgSO$_4$) and concentrated in vacuo. The residue was purified by reverse phase HPLC (YMC ODS-A 100×20 mm, 5 µm, 25 mL/min, gradient 60% to 100% (over 7 min) then 100% (3 min) MeOH in 10% MeOH/water) to give 3-(4-chlorophenyl)-1-(1-isopropylpiperidin-4-yl)-1H-pyrazolo[4,3-c]pyridine (102 mg, 35.0%) as a colourless gum.

Analytical HPLC: purity 97.2% (System B, R$_T$=3.98 min); Analytical LCMS: purity 100% (System B, R$_T$=4.05 min), ES$^+$: 355.5 [$^{35}$ClMH]$^+$ and 357.5 [$^{37}$ClMH]$^+$; HRMS calcd for C$_{20}$H$_{23}$ClN$_4$: 354.1611. found 354.1628.

Example 17

3-(4-Fluorophenyl)-1-(1-methylpiperidin-4-yl)-1H-pyrazolo[4,3-c]pyridine

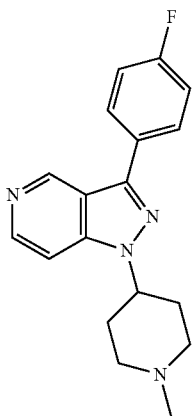 [SMILES: CN1CCC(n2nc(-c3ccc(F)cc3)c3cnccc32)CC1]

Intermediate 2 (200 mg, 0.94 mmol) and triphenylphosphine (369 mg, 1.41 mmol) were suspended in DCM (5 mL) and 4-hydroxy-1-methylpiperidine (162 mg, 1.41 mmol) and DIAD (277 µL, 1.41 mmol) were added. The reaction mixture was stirred for 3 d and concentrated in vacuo. The residue was suspended in 1 M HCl (50 mL), washed with DCM (2×30 mL), basified with NaOH and extracted with DCM (3×50 mL). The combined organic extracts were dried (MgSO$_4$) and concentrated in vacuo. The residue was purified by reverse phase HPLC (YMC ODS-A 100×20 mm, 5 µm, 25 mL/min, gradient 60% to 100% (over 7 min) then 100% (3 min) MeOH in 10% MeOH/water) to give 3-(4-fluorophenyl)-1-(1-methylpiperidin-4-yl)-1H-pyrazolo[4,3-c]pyridine as a pale yellow gum (35 mg, 12.0%).

Analytical HPLC: purity 99.5% (System B, R$_T$=3.50 min); Analytical LCMS: purity 100% (System B, R$_T$=3.51 min), ES$^+$: 311.5 [MH]$^+$; HRMS calcd for C$_{18}$H$_{19}$FN$_4$: 310.1594. found 310.1602.

Example 18

3-(4-Fluorophenyl)-1-piperidin-4-yl-1H-pyrazolo[4,3-c]pyridine

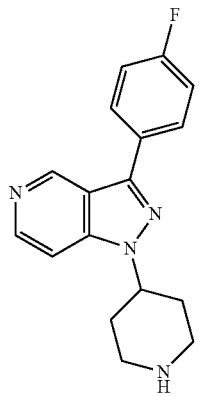 [SMILES: Fc1ccc(-c2nn(C3CCNCC3)c3ccncc23)cc1]

Intermediate 2 (200 mg, 0.94 mmol) and PPh$_3$ (369 mg, 1.41 mmol) were suspended in DCM (5 mL). N-Boc-4-hydroxypiperidine (283 mg, 1.41 mmol) and DIAD (277 µL, 1.41 mmol) were added. The reaction mixture was stirred for 3 d, TFA (2 mL) was added and the reaction mixture was stirred for 3 h and concentrated in vacuo. The residue was suspended in 1 M HCl (50 mL), washed with DCM (2×30 mL), basified with NaOH and extracted with DCM (3×50 mL). The combined organic extracts were dried (MgSO$_4$) and concentrated in vacuo. The residue was purified by reverse phase HPLC (YMC ODS-A 100×20 mm, 5 µm, 25 mL/min, gradient 40% to 80% (over 7 min) then 100% (3 min) MeOH in 10% MeOH/water and YMC ODS-A 100×20 mm, 5 µm, 15 mL/min, gradient 0% to 40% (over 12 min) then 100% (3 min) MeOH+1% HCO$_2$H in 10% MeOH/water+1% HCO$_2$H). The purified fractions were concentrated in vacuo by half, poured into 1 M aq Na$_2$CO$_3$ solution (50 mL) and extracted with DCM (3×50 mL). The combined organic layers were dried (MgSO$_4$) and concentrated in vacuo to give 3-(4-fluorophenyl)-1-piperidin-4-yl-1H-pyrazolo[4,3-c]pyridine as a colourless gum (67 mg, 24.1%).

Analytical HPLC: purity 99.1% (System B, $R_T$=3.44 min); Analytical LCMS: purity 100% (System B, $R_T$=3.48 min), ES$^+$: 297.6 [MH]$^+$; HRMS calcd for $C_{17}H_{17}FN_4$: 296.1437. found 296.1449.

Example 19

4-[1-(Tetrahydro-2H-pyran-4-yl)-1H-pyrazolo[4,3-c]pyridin-3-yl]benzonitrile

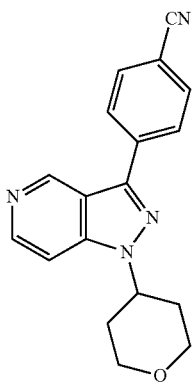

Intermediate 4 (275 mg, 1.25 mmol) and PPh$_3$ (490 mg, 1.87 mmol) were suspended in DCM (5 mL) and 4-hydroxytetrahydropyran (178 μL, 1.87 mmol) and DIAD (368 μL, 1.87 mmol) were added. The reaction mixture was stirred for 18 h and concentrated in vacuo. The residue was purified by reverse phase HPLC (YMC ODS-A 100×20 mm, 5 μm, 25 mL/min, gradient 40% to 80% (over 7 min) then 100% (3 min) MeOH in 10% MeOH/water) and by column chromatography (normal phase, 20 g, Strata SI-1, silica gigatube, heptane/EtOAc (1:1) (300 mL) then EtOAc (500 mL)) to give 4-[1-(tetrahydro-2H-pyran-4-yl)-1H-pyrazolo[4,3-c]pyridin-3-yl]benzonitrile as a white solid (140 mg, 36.8%).

Analytical HPLC: purity 99.9% (System B, $R_T$=4.61 min); Analytical LCMS: purity 100% (System B, $R_T$=4.33 min), ES$^+$: 305.5 [MH]$^+$; HRMS calcd for $C_{18}H_{16}N_4O$: 304.1324. found 304.1334.

Example 20

4-[1-(1-Methylpiperidin-4-yl)-1H-pyrazolo[4,3-c]pyridin-3-yl]benzonitrile

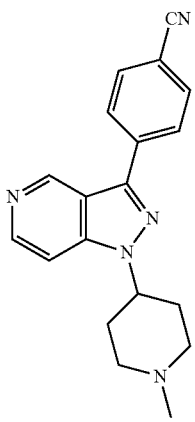 [SMILES: CN1CCC(n2nc(-c3ccc(C#N)cc3)c3cnccc32)CC1]

Intermediate 4 (275 mg, 1.25 mmol) and PPh$_3$ (490 mg, 1.87 mmol) were suspended in DCM (5 mL) and 4-hydroxy-1-methylpiperidine (216 mg, 1.87 mmol) and DIAD (368 μL, 1.87 mmol) were added. The reaction mixture was stirred for 18 h and concentrated in vacuo. The residue was dissolved in MeOH (5 mL), poured into 1 M aq Na$_2$CO$_3$ solution (50 mL) and extracted with DCM (2×50 mL). The aq layer was basified with NaOH and extracted with EtOAc (3×50 mL). The combined organic layers were dried (MgSO$_4$) and concentrated in vacuo. The residue was purified by column chromatography (normal phase, 20 g, Strata SI-1, silica gigatube, DCM/EtOH/NH$_3$ 200:8:1 (300 mL) then DCM/EtOH/NH$_3$ 100:8:1 (500 mL)) and by reverse phase HPLC (YMC ODS-A 100×20 mm, 5 μm, 15 mL/min, gradient 0% to 30% (over 12 mM) then 100% (3 min) MeOH+1% formic acid in 10% MeOH/water+1% formic acid). The residue was dissolved in 1 M aq Na$_2$CO$_3$ solution (25 mL), extracted with DCM (2×25 mL), dried (MgSO$_4$) and concentrated in vacuo to give 4-[1-(1-methylpiperidin-4-yl)-1H-pyrazolo[4,3-c]pyridin-3-yl]benzonitrile as a white solid (46 mg, 12.6%).

Analytical HPLC: purity 99.5% (System B, $R_T$=3.34 min); Analytical LCMS: purity 100% (System B, $R_T$=3.31 min), ES$^+$: 318.5 [MH]$^+$; HRMS calcd for $C_{19}H_{19}N_5$: 317.1640. found 317.1649.

Biological Tests

Biological Assay of the SSAO Enzyme Inhibitors

All assays were performed in room temperature with purified recombinantly expressed human SSAO. Enzyme was prepared essentially as described in Öhman et al. (*Protein Expression and Purification* 2006, 46, 321-331). The enzyme activity was measured with benzylamine as substrate and utilized the production of hydrogen peroxide for detection. In a horseradish peroxidise (HRP) coupled reaction, hydrogen peroxide oxidation of 10-acetyl-3,7-dihydroxyphenoxazine produced resorufin, which is a highly fluorescent compound (Zhout and Panchuk-Voloshina. *Analytical Biochemistry* 1997, 253, 169-174; Amplex® Red Hydrogen Peroxide/peroxidise Assay kit, Invitrogen A22188).

Briefly, test compounds were dissolved in dimethyl sulfoxide (DMSO) to a concentration of 10 mM. Dose-response measurements were assayed by either creating 1:10 serial dilutions in DMSO to produce a 7 point curve or by making 1:3 serial dilutions in DMSO to produce 11 point curves. The top concentrations were adjusted depending on the potency of the compounds and subsequent dilution in reaction buffer (50 mM sodium phosphate, pH 7.4) yielded a final DMSO concentration≤2%. Enzyme and compounds were set to pre-incubate in flat-bottomed microtiter plates for approximately 60 minutes before initiating the reaction by addition of a mixture of HRP, benzylamine and Amplex reagent. Fluorescence intensity was then measured at several time points (15 minutes, 20 minutes and 30 minutes) exciting at 544 nm and reading the emission at 590 nm). Final concentrations of the reagents in the assay wells were: SSAO enzyme 2 μg/ml, benzylamine 100 μM, Amplex reagent 20 μM, HRP 0.1 U/mL and varying concentrations of test compound. The inhibition was measured as % decrease of the signal compared to a control without inhibitor (only diluted DMSO). The background signal from a sample containing no SSAO enzyme was subtracted from all data points. Data was fitted to a four parameter logistic model and IC$_{50}$ values were calculated using the GraphPad Prism 4 or XLfit 4 programs.

The exemplified compounds of the invention generally had an IC$_{50}$ value of 10 to 1000 nM. Obtained IC$_{50}$ values for representative compounds are shown in the table below:

| Compound | IC$_{50}$ (nM) |
|---|---|
| Example 3 | 89 |
| Example 5 | 120 |

The invention claimed is:

1. A method for the treatment of inflammation, an inflammatory disease, an immune or an autoimmune disorder, which comprises administering to a mammal, in need of such treatment an effective amount of a compound of formula (I),

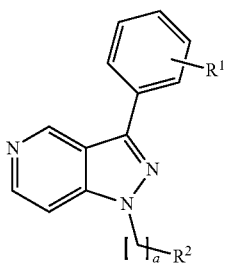

or a pharmaceutically acceptable salt, geometrical isomer, tautomer, optical isomer or N-oxide thereof, wherein:

$R^1$ is one, two or three substituents independently selected from halogen, cyano, $C_{1-6}$-alkyl, halo-$C_{1-6}$-alkyl and $C_{1-6}$-alkoxy;

$R^2$ is a 4- to 7-membered saturated or partially saturated heterocyclic ring containing, 1 or 2 heteroatoms independently selected from O, S and N($R^3$), and wherein ring carbon atoms are optionally substituted with $R^4$;

$R^3$ is selected from hydrogen, $C_{1-6}$-alkyl, hydroxy-$C_{1-6}$-alkyl, cyano-$C_{1-6}$-alkyl, halo-$C_{1-6}$-alkyl, $C_{1-6}$-alkoxy-$C_{1-6}$-alkyl, $C_{1-6}$-acyl and $C_{1-6}$-alkylsulfonyl;

$R^4$ is selected from halogen, hydroxy, $C_{1-6}$-alkyl, hydroxy-$C_{1-6}$-alkyl, $C_{1-6}$-alkoxy-$C_{1-6}$-alkyl, cyano-$C_{1-6}$-alkyl, halo-$C_{1-6}$-alkyl, and $C_{1-6}$-alkoxy; and a is 0, 1 or 2;

provided that the compound is not:
3-(3,4-dichlorophenyl)-1-(1-methylpiperidin-4-yl)-1H-pyrazolo[4,3-c]pyridine, or
1-(1-methylpiperidin-4-yl)-3-[4-(trifluoromethyl)phenyl]-1H-pyrazolo[4,3-c]pyridine.

2. The method according to claim 1, wherein the inflammation or inflammatory disease or immune or autoimmune disorder is arthritis, synovitis, vasculitis, a condition associated with inflammation of the bowel, atherosclerosis, multiple sclerosis, Alzheimer's disease, vascular dementia, a pulmonary inflammatory disease, a fibrotic disease, an inflammatory disease of the skin, systemic inflammatory response syndrome, sepsis, an inflammatory and/or autoimmune condition of the liver, diabetes (type I or II) and/or the complications thereof, chronic heart failure, congestive heart failure, an ischemic disease or myocardial infarction and/or the complications thereof.

3. The method according to claim 1, wherein the inflammatory disease is vasculitis.

4. The method according to claim 1, wherein the inflammation or inflammatory disease or immune or autoimmune disorder is rheumatoid arthritis, juvenile rheumatoid arthritis, osteoarthritis, psoriatic arthritis, Crohn's disease, ulcerative colitis, inflammatory bowel disease, irritable bowel syndrome, asthma, chronic obstructive pulmonary disease, acute respiratory distress syndrome, idiopathic pulmonary fibrosis, cardiac fibrosis, systemic sclerosis, contact dermatitis, atopic dermatitis, psoriasis, autoimmune hepatitis, primary biliary cirrhosis, alcoholic liver disease, sclerosing cholangitis, autoimmune cholangitis, stroke, or ischemia-reperfusion injury.

5. The method according to claim 1 wherein the compound has formula (I'),

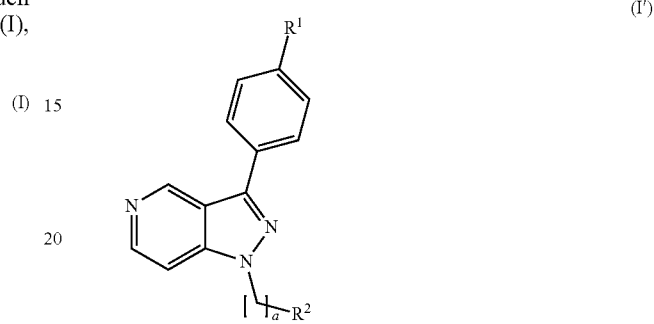

wherein $R^1$ is selected from halogen, cyano and $C_{1-4}$-alkyl;

$R^2$ is a 5- to 6-membered saturated or partially saturated heterocyclic ring containing 1 or 2 heteroatoms independently selected from O, S and N($R^3$), and wherein ring carbon atoms are optionally substituted with $R^4$;

$R^3$ is selected from hydrogen, $C_{1-4}$-alkyl, hydroxy-$C_{1-4}$-alkyl, cyano-$C_{1-4}$-alkyl, halo-$C_{1-4}$-alkyl, $C_{1-4}$-alkoxy-$C_{1-4}$-alkyl, $C_{1-4}$-acyl and $C_{1-4}$-alkylsulfonyl;

$R^4$, if present, is independently selected from $C_{1-4}$-alkyl, halo-$C_{1-4}$-alkyl, hydroxy-$C_{1-4}$-alkyl and $C_{1-4}$-alkoxy-$C_{1-4}$-alkyl; and a is 0 or 1.

6. The method according to claim 1 wherein the compound has formula (I''),

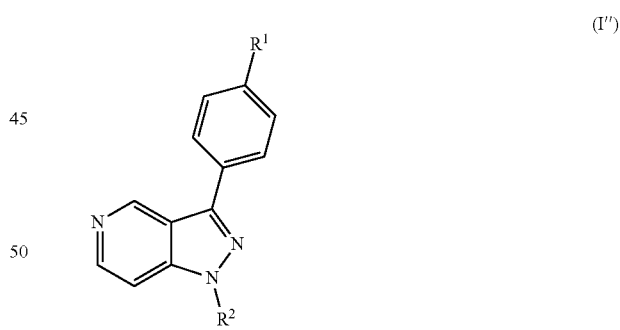

wherein $R^1$ is selected from halogen, cyano and $C_{1-4}$-alkyl;

$R^2$ is a saturated 5- to 6-membered heterocyclic ring containing 1 heteroatom selected from O and N($R^3$), and wherein ring carbon atoms are optionally substituted with $R^4$;

$R^3$ is hydrogen, $C_{1-4}$-alkyl or cyano-$C_{1-4}$-alkyl; and $R^4$, if present, is independently methyl or ethyl.

7. The method according to claim 1 wherein the compound is selected from:
3-(4-Fluorophenyl)-1-(tetrahydro-2H-pyran-4-yl)-1H-pyrazolo[4,3-c]pyridine;
3-(4-Chlorophenyl)-2-(tetrahydro-2H-pyran-4-yl)-2H-pyrazolo[4,3-c]pyridine;

3-(4-Methylphenyl)-1-(tetrahydro-2H-pyran-4-yl)-1H-pyrazolo[4,3-c]pyridine;
3-(4-Chlorophenyl)-1-[(3R)-tetrahydrofuran-3-yl]-1H-pyrazolo[4,3-c]pyridine;
3-(4-Chlorophenyl)-1-piperidin-4-yl-1H-pyrazolo[4,3-c]pyridine;
3-(4-Chlorophenyl)-1-(1-methylpiperidin-4-yl)-1H-pyrazolo[4,3-c]pyridine;
{4-[3-(4-Chlorophenyl)-1H-pyrazolo[4,3-c]pyridin-1-yl]piperidin-1-yl}acetonitrile;
3-(4-Chlorophenyl)-1-(tetrahydro-2H-pyran-4-ylmethyl)-1H-pyrazolo[4,3-c]pyridine;
3-(4-Chlorophenyl)-1-[1-(methylsulfonyl)piperidin-4-yl]-1H-pyrazolo[4,3-c]pyridine;
1-(1-Acetylpiperidin-4-yl)-3-(4-chlorophenyl)-1H-pyrazolo[4,3-c]pyridine;
3-(4-Chlorophenyl)-1-[1-(2-methoxyethyl)piperidin-4-yl]-1H-pyrazolo[4,3-c]pyridine;
3-(4-Chlorophenyl)-1-piperidin-3-yl-1H-pyrazolo[4,3-c]pyridine;
3-(4-Chlorophenyl)-1-[(3S)-tetrahydrofuran-3-yl]-1H-pyrazolo[4,3-c]pyridine;
3-(4-Chlorophenyl)-1-(tetrahydrofuran-3-ylmethyl)-1H-pyrazolo[4,3-c]pyridine;
3-(4-Chlorophenyl)-1-(1-ethylpiperidin-4-yl)-1H-pyrazolo[4,3-c]pyridine;
3-(4-Chlorophenyl)-1-(1-isopropylpiperidin-4-yl)-1H-pyrazolo[4,3-c]pyridine;
3-(4-Fluorophenyl)-1-(1-methylpiperidin-4-yl)-1H-pyrazolo[4,3-c]pyridine;
3-(4-Fluorophenyl)-1-piperidin-4-yl-1H-pyrazolo[4,3-c]pyridine;
4-[1-(Tetrahydro-2H-pyran-4-yl)-1H-pyrazolo[4,3-c]pyridin-3-yl]benzonitrile; and
4-[1-(1-Methylpiperidin-4-yl)-1H-pyrazolo[4,3-c]pyridin-3-yl]benzonitrile.

\* \* \* \* \*